United States Patent [19]

Backerud

[11] Patent Number: 5,373,888
[45] Date of Patent: Dec. 20, 1994

[54] METHOD FOR THE PRODUCTION OF DUCTILE CAST IRON

[75] Inventor: Stig L. Backerud, Bloomfield Hills, Minn.

[73] Assignee: SinterCast AB, Stockholm, Sweden

[21] Appl. No.: 39,126

[22] PCT Filed: Oct. 11, 1991

[86] PCT No.: PCT/SE91/00686

§ 371 Date: Apr. 15, 1993

§ 102(e) Date: Apr. 15, 1993

[87] PCT Pub. No.: WO92/06810

PCT Pub. Date: Apr. 30, 1992

[30] Foreign Application Priority Data

Oct. 15, 1990 [SE] Sweden .................. 9003290-5

[51] Int. Cl.⁵ .................. B22D 2/00; C21C 1/10
[52] U.S. Cl. .................. 164/4.1; 75/377; 420/31; 164/57.1
[58] Field of Search .................. 164/4.1, 150, 154; 75/377, 376, 10.46; 266/79, 99; 374/26; 420/31

[56] References Cited

U.S. PATENT DOCUMENTS

| | | | |
|---|---|---|---|
| 4,046,509 | 9/1977 | Bäckerud | 164/4.1 |
| 4,261,740 | 4/1981 | Plessers | 75/129 |
| 4,333,512 | 6/1982 | Sugiura | 164/150 |
| 4,354,391 | 10/1982 | Li | 164/4.1 |
| 4,358,948 | 11/1982 | Plessers | 374/26 |
| 4,667,725 | 5/1987 | Backerud | 264/4.1 |
| 4,696,337 | 9/1987 | Grochal | 164/150 |
| 4,765,391 | 8/1988 | Backerud | 164/150 |

FOREIGN PATENT DOCUMENTS

| | | | |
|---|---|---|---|
| 0157308 | 10/1985 | European Pat. Off. | G01N 25/04 |
| 0287391 | 2/1991 | Germany | 164/4.1 |
| 3101050 | 5/1988 | Japan | 164/4.1 |

*Primary Examiner*—P. Austin Bradley
*Assistant Examiner*—Erik R. Puknys
*Attorney, Agent, or Firm*—Cushman, Darby & Cushman

[57] ABSTRACT

During production of ductile cast iron, controlling and correcting the composition of the cast iron melt, including extracting a sample from the melt, the mother melt, and adding an amount of an oxide, a sulphite or an oxy-sulphide with the ability to oxidize an amount of the modifying agent present in the sample and corresponding to the fading rate expected to occur during the casting process as a whole. The sample is permitted to solidify in a sample vessel equipped with two thermocouples, one in the center of the sample vessel and the other in the vicinity of the sample vessel wall. The temperature and time are recorded during the process of solidification in a manner known per se and nodularity is calculated. If the amount of modifying agent is too low to secure a fully nodular graphite throughout the whole casting period, an appropriate amount of modifying agent is added.

6 Claims, 2 Drawing Sheets

METHOD FOR THE PRODUCTION OF DUCTILE CAST IRON

BACKGROUND OF THE INVENTION

The present invention relates to a method for the production of ductile cast iron, comprising controlling and correcting the composition and physical properties of the cast iron melt. More particularly, the method comprises the steps of determining the inherent structural characteristics of the melt by thermal melt analysis and making corrections that are necessary.

Thermal analysis has long been applied for determining the characteristics of metal melts. The thermal analysis method allows a sample of the melt to be solidified in a suitable vessel provided with one or more thermocouples by means of which the temperatures which prevail as the sample solidifies are recorded. The precipitation of different phases and phase transformations can be seen from the temperature-time curves.

In the production of ductile iron, it is essential that the amount of structure modifying agent present is sufficient to provide nodular graphite precipitation. There must, of course, also be a sufficient amount of nucleating agent present.

U.S. Pat. No. 4,667,725 teaches a method of determining the structure characteristics of a melt which will permit determination of the metallographic structure which develops during the solidification of a metal melt. The method comprises extracting a sample from the melt and permitting the melt to solidify in a sample vessel provided with two thermosensors, one of which is placed in the centre of the sample volume and the other of which is placed in the vicinity of the inner wall of the sample vessel. During the process of solidification, the various temperatures in time are recorded through both thermosensors. From these recordings, values of miniumum and maximum points, duration of level temperatures, shoulders, derivatives, etc. are used to predict the structure characteristics that will be obtained. The method according to U.S. Pat. No. 4,667,725 is mainly directed to the production of compacted cast iron, which has been a challenging task for the person skilled in this art. However, this technique can also be used to predict the structure characteristics of a melt intended for casting ductile cast iron. A typical melt for casting ductile cast iron has a C.E. value of 4.4–4.6, i.e. a hypereutectic cast iron. The method will only disclose that nodular graphite solidification will be obtained. No information relating to excessive amounts of structure modifying agent can be obtained. This means that even if the amount of modifying agent is sufficient to obtain a good cast product at the moment of extracting the sample, the modifying agent content may have decreased, by fading or burning-off, during the process of casting and thus the moulds that are filled last may possibly receive a cast iron melt which contains insufficient amounts of modifying agent.

Fading is contingent on the actual process applied and the particular production equipment used. For example, in one particular foundry, fading was established to be 0.003% Mg with each 5 minute period. The casting period was about 15 minutes in this case. In other words, the modifying agent content (in this case the magnesium content) was found to decrease by a total of 0.009% during the whole casting period.

The above-mentioned problem has forced the foundryworker to use a relatively high excess of modifying agent, so as to guarantee a completely nodular graphite cast iron throughout each production run. The use of an excess quantity of modifying agent, such as magnesium, has the following drawbacks:

1. It makes the process more expensive;
2. It increases the tendency to produce residual carbide formations; and
3. It may form unwanted oxide inclusions in the castings.

There is an apparent need for a method which will allow the addition of modifying agent, such as magnesium and corresponding metals to be decreased.

SUMMARY OF THE INVENTION

The present invention enables the need for a modifying agent to be diminished without risk of obtaining castings in which the graphite is not completely in nodular form.

The invention provides in a method for the production of ductile cast iron, by carefully controlling and correcting the composition and inherent physical properties of the cast iron melt. The method comprises extracting a sample from a melt intended for casting ductile cast iron. This melt will contain a modifying agent in a quantity which is at least enough to create nodular graphite when solidifying. Excess amounts of modifying agent should be avoided. A melt sample is introduced into a sample vessel, which is permitted to come into thermal equilibrium with the melt. The sample vessel is provided with two thermosensors, one of which is positioned so as to be in the centre of the sample volume and the other of which is positioned so as to be in the vicinity of the wall of the sample vessel. The sample melt contained in the vessel is permitted to solidify and the temperature values prevailing during the process of solidification are recorded through the thermosensors. As thermosensors can i.a. thermocouples or pyrometers be used.

According to one embodiment of the invention, a given quantity of an oxide, a sulphide or an oxysulphide is added, in an amount which is sufficient to oxidize the modifying agent present in the sample, so as to lower the percentage of modifying agent present by about 0.01% (calculated for magnesium).

The modifying agent is of a type known to the person skilled in this art. Normally, magnesium is used, often in combination with rare earth metals, although other agents may also be used. For the sake of simplicity, I refer here to a modifying agent consisting solely of magnesium, which makes it possible to give realistic percentage figures. The person skilled in this art will immediately realize the corrections that are required when using other modifying agents.

According to the present invention, a determined amount of an oxidizing agent is added to the sample vessel. This oxidizing agent will react with the melt sample, which is a determined volume dependent on the design of the sample vessel used, by oxidizing the modifying agent, usually magnesium. This oxidizing action reduces the content of active modifying agent by a predetermined percentage which is calculated to correspond to the loss of active modifying agent due to fading during the normal time of the casting process.

It is also possible to extract a melt sample with a ladle and then add an appropriate amount of oxidating agent to the ladle. The sample vessel can then be submerged in the ladle and filled with melt. The sample vessel is thereafter taken up and the recording of the solidification temperatures carried out.

BRIEF DESCRIPTION OF THE INVENTION

The invention will now be explained in more detail with reference to the accompanying drawings; in which:

FIG. 1 is a graph which shows the relationship between different types of graphite precipitation, expressed in percentage of nodular graphite crystals, and the percentage of dissolved elementary magnesium; and FIG. 2 is a graph which shows a typical recording of a good ductile cast iron melt, where the amount of dissolved elementary magnesium is decreased by 0.01%.

DETAILED DESCRIPTION

Figure 1:
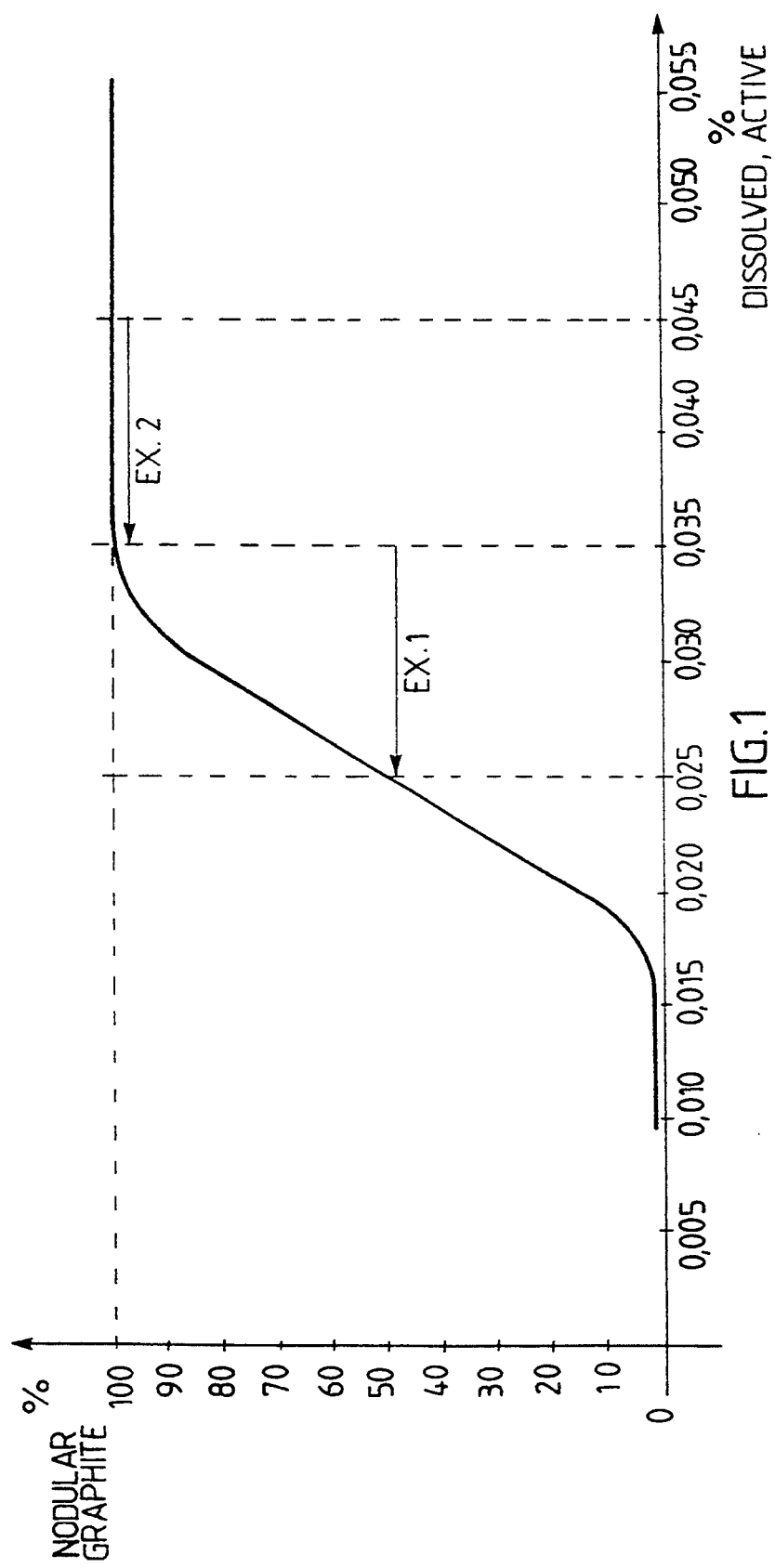

The values make it possible to predict the percentage of magnesium present when the graphite formed is not completely nodular (or compacted). This is shown in FIG. 1, which illustrates the relationship between the percentage of nodular graphite formed and the content of dissolved elementary magnesium. From FIG. 1, it can be seen that this area is from about 0.016% to 0.032% Mg and that information concerning the percentage of nodular graphite formed also informs about the percentage of dissolved elementary magnesium within this area of about 0.016–0.032% Mg. In the area above about 0.032% Mg, it is impossible to observe changes in the magnesium content from the solidification curves, while at contents below 0.016% Mg, the graphite is fully compacted until it becomes flaky below about 0.008% Mg.

Figure 2:
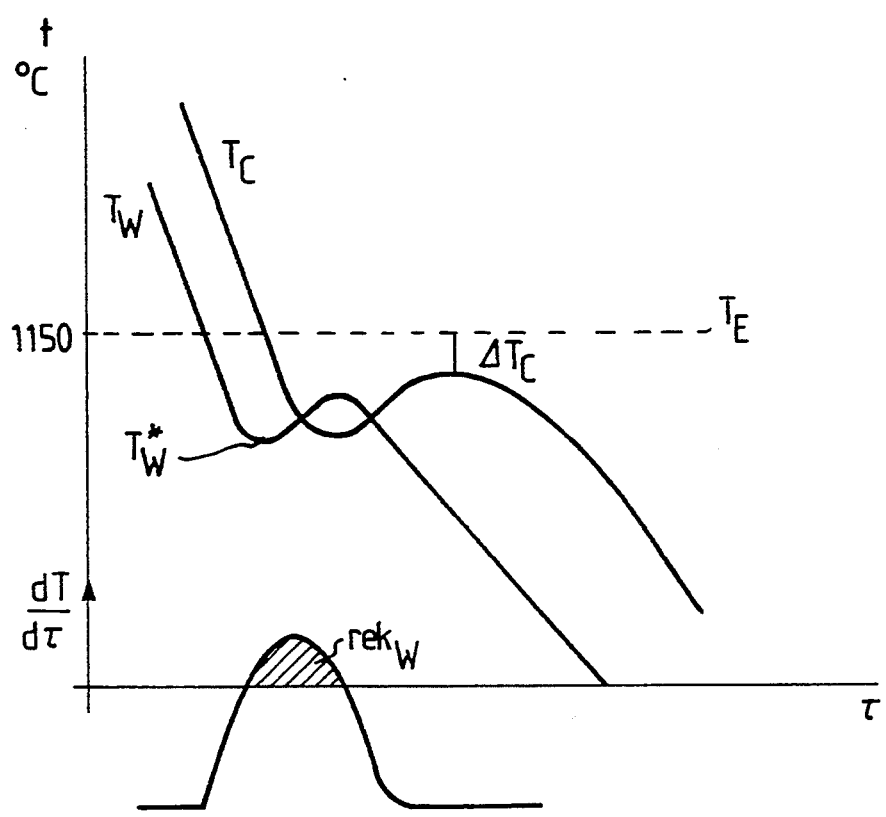

FIG. 2 shows typical curves (Tc, Tw) for an acceptable melt from which ductile cast iron can be cast. The most important values are $T^*_w$ which is the super-cooling achieved at the thermocouple located in the vicinity of the sample vessel wall, Tw, which informs about the precipitation nuclei in the melt. Of value is also the $rek_w$ value, which is the positive derivative of the solidification curve in the lower part of the diagram and the $\Delta T_c$ value which is the difference between the equilibrium eutectic temperature $T_E$ and maximum growth temperature at the centre of (the curve Tc) of the sample volume. This value $\Delta T_c$ gives information about the percentage of nodular graphite precipitations. The person skilled in this art will realize which values correspond to the equipment used.

The signal from the thermocouples is a function of the latent heat evolved during the solidification process. As the growth rate depends on the growth mechanism which in turn is influenced by the amount of modifying element present in the melt, the rate of evaluation of latent "heat" can be established as a function of the aspect ratio length divided by width of graphite crystals, from say 20/1 for a typical compacted graphite crystal, to 1/1 in the case of a fully modular crystal.

The diagram of the thermal analysis values changes in morphology is therefore at its maximum in the midst of the S-curve shown in FIG. 1 and a minima where the curve flattens out.

The invention is exemplified in the following examples, which are not intended to restrict the scope of the invention.

EXAMPLE 1

A cast iron melt was produced in which the true content of dissolved elementary magnesium was 0.035% (subsequently calculated). A thermal analysis was carried out in a known manner on a melt sample contained in a sample vessel of the kind specified in the introductory part of the specification. This analysis showed that the melt sample was of acceptable quality, with an almost complete nodularity.

It was the intention to complete the entire casting process within a time period of 15 minutes from the moment of taking a sample. Assuming that the fading rate of Mg is 0.003%/5 minutes, the true Mg-level will be 0.026% at the end of this 15-minute period and will have entered the area in which an inferior ductile iron quality with a nodularity of less than the standard 80% appears in the final castings of the series.

In the thermal analysis, carried out in accordance with the invention, the original magnesium level of the sample was reduced by 0.010% through the iron and sulphur addition, thus giving a result corresponding to 0.035–0.010=0.025% Mg and a nodularity of about 50% (cf. FIG. 1).

Thus, it is necessary to increase the Mg content of the whole melt to at least 0.042% Mg, so as to compensate for magnesium which is lost through fading during the entire process (e.g. 15 minutes). Thus, an additional amount of 0.042–0.035=0.007% Mg is necessary.

EXAMPLE 2

A cast iron melt in which the true active magnesium content was 0.055% was tested according to the present invention. The thermal analysis showed a nodularity of 100% (0.055–0.010=0.045).

The cast iron melt was intended for the production castings over a casting period of 15 minutes. No problem concerning nodularity was observed, although a metallographic analysis showed some oxide inclusions and a minor amount of carbides in the solidified sample. The test showed that the modifying agent was in excess and could be decreased in the next batch of melt. Alternatively, the magnesium content can be decreased by using a holding time before casting or by adding an appropriate amount of an oxidation agent.

Thus, the invention provides a valuable tool in the art of casting ductile cast iron products.

I claim:

1. A method for producing ductile cast iron, comprising:
    (a) providing a mother melt of molten iron containing an Mg-based structure-modifying agent for tending to cause carbon in said melt to precipitate as nodular graphite as the contents of molds filled by pouring said mother melt are allowed to solidify, despite gradual fading or burning of said structure-modifying agent, with passage of time, while said molds are being filled;
    (b) taking a sample from said mother melt into a sample vessel that has a bounding wall, and permitting the sample vessel to come into thermal equilibrium with said mother melt;
    (c) providing the sample with an amount of an oxidizing agent which is an oxide, a sulfide or an oxysulfide and has an ability to oxidize an amount of said structure-modifying agent in said sample corresponding in proportion to that which would fade or burn off from said mother melt while said molds are being filled by pouring from said mother melt assuming such pouring were to be completed during a time interval having a certain duration;

(d) permitting the sample to solidify while measuring temperatures therefrom using a first thermosensor located centrally of the vessel and a second thermosensor located near said vessel wall, and recording said temperatures;

(e) calculating from said temperatures and known correlations of temperatures, nodularity of precipitated graphite crystals in castings and percentage of active structure-modifying agent in mother melts, whether said mother melt contains an insufficient active amount of said structure-modifying agent for causing castings formed by pouring successive quantities of said mother melt from said mother melt into said molds during a period substantially equating to said duration of said time interval, to contain a predetermined acceptable amount of nodular precipitated graphite crystals as a percentage of total precipitated graphite crystals;

(f) when calculations made in step (e) indicate presence of an insufficient active amount of said structure-modifying agent in said mother melt, adjusting the active amount of said structure-modifying agent in said mother melt so as to become said sufficient amount; and (g) thereafter pouring successive quantities of said mother melt from said mother melt into molds during a period substantially equating to said duration of said time interval, and allowing the resulting contents of said molds to solidify into ductile cast iron castings having said predetermined acceptable amount of nodular precipitated graphite crystals as a percentage of total precipitated graphite crystals.

2. The method of claim 1, wherein:
said time interval is about 15 minutes and, in step (c) said amount of oxidizing agent is sufficient to oxidize, and thereby deactivate, said structure-modifying agent in said sample by 0.005–0.015% Mg, from an initial level within the range of about 0.016–0.032% Mg.

3. The method of claim 1, wherein:
steps (b) and (c) are performed by introducing at least a portion of said mother melt into a ladle; adding said oxidizing agent to said portion of said mother melt in said ladle; immersing the sample vessel in said portion of said mother melt in said ladle, thereby filling said sample vessel with said sample and permitting the sample vessel to come into the thermal equilibrium with said portion of said mother melt; and withdrawing said sample vessel, containing said sample, from said ladle.

4. The method of claim 1, wherein:
in step (e), an additional amount of said structure-modifying agent is added to said mother melt.

5. The method of claim 1, wherein:
in step (e), also calculating from said temperatures and known correlations of temperatures, nodularity of precipitated graphite crystals in castings and percentage of active structure-modifying agent in mother melts, whether said mother melt contains an excessive active amount of said structure-modifying agent for causing castings formed by pouring successive quantities of said mother melt from said mother melt into said molds during a period substantially equating to said duration of said time interval, to contain a predetermined acceptable amount of nodular precipitated graphite crystals as a percentage of total precipitated graphite crystals; and when calculations made in step (e) indicate presence of an excessive active amount of said structure-modifying agent in said mother melt, adjusting the active amount of said structure-modifying agent in said mother melt so as to become said sufficient amount.

6. The method of claim 5, wherein:
in step (e), said active amount of said structure-modifying agent is modified by adding to said mother melt an oxidizing agent which is an oxide, a sulfide or an oxysulfide.

* * * * *